United States Patent
Ovadia et al.

(10) Patent No.: US 11,847,730 B2
(45) Date of Patent: Dec. 19, 2023

(54) ORIENTATION DETECTION IN FLUOROSCOPIC IMAGES

(71) Applicant: Covidien LP, Mansfield, MA (US)

(72) Inventors: Daniel Ovadia, Ramat Gan (IL); Guy Alexandroni, Haifa (IL); Ariel Birenbaum, Raanana (IL)

(73) Assignee: COVIDIEN LP, Mansfield, MA (US)

(*) Notice: Subject to any disclaimer, the term of this patent is extended or adjusted under 35 U.S.C. 154(b) by 215 days.

(21) Appl. No.: 17/096,815

(22) Filed: Nov. 12, 2020

(65) Prior Publication Data

US 2021/0233301 A1    Jul. 29, 2021

Related U.S. Application Data

(60) Provisional application No. 62/965,668, filed on Jan. 24, 2020.

(51) Int. Cl.
*G06T 15/00* (2011.01)
*G06T 7/00* (2017.01)

(52) U.S. Cl.
CPC .......... *G06T 15/005* (2013.01); *G06T 7/0012* (2013.01); *G06T 2207/10064* (2013.01); *G06T 2207/20081* (2013.01); *G06T 2207/20084* (2013.01); *G06T 2207/30061* (2013.01)

(58) Field of Classification Search
None
See application file for complete search history.

(56) References Cited

U.S. PATENT DOCUMENTS

| | | | |
|---|---|---|---|
| 6,373,916 B1 | 4/2002 | Inoue et al. | |
| 6,473,634 B1 | 10/2002 | Barni | |
| 7,551,759 B2 | 6/2009 | Hristov et al. | |
| 7,916,918 B2 | 3/2011 | Suri et al. | |
| 8,335,359 B2 | 12/2012 | Fidrich et al. | |
| 8,396,533 B2* | 3/2013 | Barbu | A61B 34/20 |
| | | | 382/154 |
| 8,482,606 B2 | 7/2013 | Razzaque et al. | |
| 8,625,869 B2 | 1/2014 | Harder et al. | |
| 8,706,184 B2 | 4/2014 | Mohr et al. | |
| 8,827,934 B2 | 9/2014 | Chopra et al. | |
| 9,433,390 B2 | 9/2016 | Nathaniel et al. | |
| 9,833,167 B2 | 12/2017 | Cohen et al. | |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Boone J M et al: "Recognition of Chest Radiograph Orientation for Picture Archiving and Communications Systems Display Using Neural Networks", Journal of Digital Imaging, Springer-Verlag, Cham, vol. 5, No. 3, Aug. 1, 1992.

(Continued)

*Primary Examiner* — Tsung Yin Tsai
(74) *Attorney, Agent, or Firm* — WEBER ROSSELLI & CANNON LLP

(57) ABSTRACT

Systems and methods of automatic orientation detection in fluoroscopic images using deep learning enable local registration for correction of initial CT-to-body registration in Electromagnetic Navigation Bronchoscopy (ENB) systems.

17 Claims, 8 Drawing Sheets

(56) References Cited

U.S. PATENT DOCUMENTS

| | | | |
|---|---|---|---|
| 9,861,446 B2* | 1/2018 | Lang | A61B 17/157 |
| 9,888,898 B2 | 2/2018 | Imagawa et al. | |
| 9,918,659 B2 | 3/2018 | Chopra et al. | |
| 10,127,629 B2 | 11/2018 | Razzaque et al. | |
| 10,130,316 B2 | 11/2018 | Funabasama et al. | |
| 10,373,719 B2 | 8/2019 | Soper et al. | |
| 10,376,178 B2 | 8/2019 | Chopra | |
| 10,405,753 B2 | 9/2019 | Sorger | |
| 10,478,162 B2 | 11/2019 | Barbagli et al. | |
| 10,480,926 B2 | 11/2019 | Froggatt et al. | |
| 10,524,866 B2 | 1/2020 | Srinivasan et al. | |
| 10,555,788 B2 | 2/2020 | Panescu et al. | |
| 10,610,306 B2 | 4/2020 | Chopra | |
| 10,638,953 B2 | 5/2020 | Duindam et al. | |
| 10,674,970 B2 | 6/2020 | Averbuch et al. | |
| 10,682,070 B2 | 6/2020 | Duindam | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,818,019 B2* | 10/2020 | Piat | G06T 7/33 |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 10,896,506 B2* | 1/2021 | Zhao | A61B 6/487 |
| 11,399,895 B2* | 8/2022 | Soper | A61B 6/487 |
| 2003/0013972 A1 | 1/2003 | Makin | |
| 2006/0110021 A1 | 5/2006 | Luo et al. | |
| 2009/0062641 A1* | 3/2009 | Barbu | A61B 34/20 |
| | | | 600/476 |
| 2013/0303945 A1 | 11/2013 | Blumenkranz et al. | |
| 2014/0035798 A1 | 2/2014 | Kawada et al. | |
| 2014/0051986 A1* | 2/2014 | Zhao | A61B 1/000094 |
| | | | 600/424 |
| 2014/0343401 A1* | 11/2014 | Huber | A61B 5/7289 |
| | | | 600/407 |
| 2015/0148690 A1 | 5/2015 | Chopra et al. | |
| 2015/0265368 A1 | 9/2015 | Chopra et al. | |
| 2016/0157939 A1 | 6/2016 | Larkin et al. | |
| 2016/0163045 A1* | 6/2016 | Penney | G06T 15/20 |
| | | | 382/131 |
| 2016/0183841 A1 | 6/2016 | Duindam et al. | |
| 2016/0192860 A1 | 7/2016 | Allenby et al. | |
| 2016/0287344 A1 | 10/2016 | Donhowe et al. | |
| 2017/0112576 A1 | 4/2017 | Coste-Maniere et al. | |
| 2017/0209071 A1 | 7/2017 | Zhao et al. | |
| 2017/0258526 A1* | 9/2017 | Lang | H05K 999/99 |
| 2017/0265952 A1 | 9/2017 | Donhowe et al. | |
| 2017/0311844 A1 | 11/2017 | Zhao et al. | |
| 2017/0319165 A1 | 11/2017 | Averbuch | |
| 2017/0372477 A1* | 12/2017 | Penney | G06T 7/0012 |
| 2018/0078318 A1 | 3/2018 | Barbagli et al. | |
| 2018/0153621 A1 | 6/2018 | Duindam et al. | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263706 A1 | 9/2018 | Averbuch | |
| 2018/0279852 A1 | 10/2018 | Rafii-Tari et al. | |
| 2018/0325419 A1 | 11/2018 | Zhao et al. | |
| 2019/0000559 A1 | 1/2019 | Berman et al. | |
| 2019/0000560 A1 | 1/2019 | Berman et al. | |
| 2019/0005687 A1* | 1/2019 | Weingarten | G06T 15/08 |
| 2019/0008413 A1 | 1/2019 | Duindam et al. | |
| 2019/0038365 A1* | 2/2019 | Soper | A61B 6/547 |
| 2019/0050999 A1* | 2/2019 | Piat | G06T 7/337 |
| 2019/0065209 A1 | 2/2019 | Mishra et al. | |
| 2019/0105007 A1* | 4/2019 | Kedmi-Shahar | A61B 6/487 |
| 2019/0110839 A1 | 4/2019 | Rafii-Tari et al. | |
| 2019/0175062 A1 | 6/2019 | Rafii-Tari et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0239837 A1* | 8/2019 | Barak | G06T 7/30 |
| 2019/0239838 A1* | 8/2019 | Barak | A61B 90/36 |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0272634 A1 | 9/2019 | Li et al. | |
| 2019/0298160 A1 | 10/2019 | Ummalaneni et al. | |
| 2019/0298451 A1 | 10/2019 | Wong et al. | |
| 2019/0320878 A1 | 10/2019 | Duindam et al. | |
| 2019/0320937 A1 | 10/2019 | Duindam et al. | |
| 2019/0336238 A1 | 11/2019 | Yu et al. | |
| 2019/0343424 A1 | 11/2019 | Blumenkranz et al. | |
| 2019/0350659 A1 | 11/2019 | Wang et al. | |
| 2019/0365199 A1 | 12/2019 | Zhao et al. | |
| 2019/0365479 A1 | 12/2019 | Rafii-Tari | |
| 2019/0365486 A1 | 12/2019 | Srinivasan et al. | |
| 2019/0380787 A1 | 12/2019 | Ye et al. | |
| 2020/0000319 A1 | 1/2020 | Saadat et al. | |
| 2020/0000526 A1 | 1/2020 | Zhao | |
| 2020/0008655 A1 | 1/2020 | Schlesinger et al. | |
| 2020/0030044 A1 | 1/2020 | Wang et al. | |
| 2020/0030461 A1 | 1/2020 | Sorger | |
| 2020/0038750 A1 | 2/2020 | Kojima | |
| 2020/0043207 A1 | 2/2020 | Lo et al. | |
| 2020/0046431 A1 | 2/2020 | Soper et al. | |
| 2020/0046436 A1 | 2/2020 | Tzeisler et al. | |
| 2020/0054399 A1 | 2/2020 | Duindam et al. | |
| 2020/0060771 A1 | 2/2020 | Lo et al. | |
| 2020/0069192 A1 | 3/2020 | Sanborn et al. | |
| 2020/0077870 A1 | 3/2020 | Dicarlo et al. | |
| 2020/0078095 A1 | 3/2020 | Chopra et al. | |
| 2020/0078103 A1 | 3/2020 | Duindam et al. | |
| 2020/0085514 A1 | 3/2020 | Blumenkranz | |
| 2020/0109124 A1 | 4/2020 | Pomper et al. | |
| 2020/0129045 A1 | 4/2020 | Prisco | |
| 2020/0129239 A1 | 4/2020 | Bianchi et al. | |
| 2020/0138515 A1 | 5/2020 | Wong | |
| 2020/0155116 A1 | 5/2020 | Donhowe et al. | |
| 2020/0170623 A1 | 6/2020 | Averbuch | |
| 2020/0170720 A1 | 6/2020 | Ummalaneni | |
| 2020/0179058 A1 | 6/2020 | Barbagli et al. | |
| 2020/0188028 A1* | 6/2020 | Feiner | G06F 3/013 |
| 2020/0188038 A1 | 6/2020 | Donhowe et al. | |
| 2020/0205903 A1 | 7/2020 | Srinivasan et al. | |
| 2020/0205904 A1 | 7/2020 | Chopra | |
| 2020/0214664 A1 | 7/2020 | Zhao et al. | |
| 2020/0229679 A1 | 7/2020 | Zhao et al. | |
| 2020/0242767 A1* | 7/2020 | Zhao | A61B 34/30 |
| 2020/0275860 A1 | 9/2020 | Duindam | |
| 2020/0297442 A1 | 9/2020 | Adebar et al. | |
| 2020/0315554 A1 | 10/2020 | Averbuch et al. | |
| 2020/0330795 A1 | 10/2020 | Sawant et al. | |
| 2020/0352427 A1 | 11/2020 | Deyanov | |
| 2020/0364865 A1 | 11/2020 | Donhowe et al. | |
| 2021/0012514 A1* | 1/2021 | Piat | G06T 19/20 |

FOREIGN PATENT DOCUMENTS

| | | | |
|---|---|---|---|
| CZ | 486540 | 9/2016 | |
| CZ | 2709512 | 8/2017 | |
| CZ | 2884879 | 1/2020 | |
| EP | 3355273 A1 * | 8/2018 | G06K 9/66 |
| EP | 3413830 A4 | 9/2019 | |
| EP | 3355273 B1 | 11/2019 | |
| EP | 3478161 A4 | 2/2020 | |
| EP | 3641686 A2 | 4/2020 | |
| EP | 3644885 A1 | 5/2020 | |
| EP | 3644886 A1 | 5/2020 | |
| JP | 6425396 B2 | 11/2018 | |
| MX | PA03005028 A | 1/2004 | |
| MX | 225663 B | 1/2005 | |
| MX | 226292 | 2/2005 | |
| MX | 246862 B | 6/2007 | |

(56) References Cited

FOREIGN PATENT DOCUMENTS

MX      265247       3/2009
MX      284569 B     3/2011

OTHER PUBLICATIONS

Partial European Search report issued in European Patent Application No. 21152879.9 dated Jun. 4, 2021, 16 pages.
Extended European Search Report issued in European Application No. 21152879.9 dated Sep. 6, 2021.

* cited by examiner

ORIENTATION DETECTION IN FLUOROSCOPIC IMAGES

CROSS REFERENCE TO RELATED APPLICATION

This application claims the benefit of and priority to U.S. Provisional Application No. 62/965,668 filed Jan. 24, 2020.

FIELD

This disclosure relates to the field of imaging, and particularly to orientation detection in fluoroscopic images.

BACKGROUND

A fluoroscopic imaging device is commonly located in the operating room during navigation procedures. In the navigation procedures, various CT cross-section views, 3D views, and/or guidance instructions may be displayed to help a clinician direct the navigation catheter to one or more targets along pre-planned pathways until the navigation catheter is aligned to the one or more targets. During the navigation procedures, a local registration may be performed to more accurately display the position of the navigation catheter with respect to the one or more targets. In order to perform the local registration, a fluoroscopy sweep of the patient is acquired and processed. A sweep video is then used to reconstruct the volume around the target in order to obtain the relationship between the target and the navigation catheter.

During setup of the fluoroscope for the local registration, the fluoroscope is positioned above the patient, a fluoroscopic image is captured, the orientation of the fluoroscopic image is determined and manually set by the clinician by selecting appropriate image labels corresponding to the orientation of the patient's body in the fluoroscopic image. However, this step complicates the local registration process, especially when different fluoroscopes having different settings are used. This manual step is also prone to human error. Therefore, there is a need for a method which can provide a fast, accurate, and robust method for detecting the orientation of a patient's body in fluoroscopic images.

SUMMARY

In one aspect, this disclosure features a method of performing local registration in a medical device navigation procedure. The method includes acquiring fluoroscopic images of at least one anatomic feature and a medical device in a patient's body captured by a fluoroscopic imaging device, processing the fluoroscopic images by a neural network to determine the orientation of the patient's body in the fluoroscopic images based on the processing of the fluoroscopic images by the neural network, and generating a three-dimensional (3D) reconstruction of the fluoroscopic images based on at least the determined orientation of the patient's body in the fluoroscopic images.

Implementations may include one or more of the following features. The fluoroscopic images may be captured by performing a fluoroscopic sweep with the fluoroscopic imaging device, and each of the fluoroscopic images from the fluoroscopic sweep may be processed using the neural network. The results of the processing may be combined to determine the orientation of the patient's body in the fluoroscopic images. The processing may include, for each fluoroscopic image of the fluoroscopic images, generating a probability value for orientation candidates and selecting the orientation candidate having the highest probability value. The orientation candidates may be four flip candidates. The at least one anatomic feature may be a sub-anatomical region. The method may include acquiring position information of the medical device in the sub-anatomical region from an electromagnetic sensor disposed on the medical device, identifying the sub-anatomical region based on the position information, and processing the fluoroscopic images by a trained neural network based on the identified sub-anatomical region to determine the orientation of the patient's body in the fluoroscopic images.

The fluoroscopic images may form a portion of a fluoroscopic sweep. A subset of the fluoroscopic images is processed by the neural network. The method may include resizing the fluoroscopic images. The sub-anatomical region may be a lobe of a lung. The medical device may be a navigation catheter and the electromagnetic sensor may form part of the electromagnetic navigation system. The neural network may be a convolutional neural network including convolutional layers, batch normalization layers, rectified linear unit layers, maximum pooling layers, an average pooling layer, and a fully connected layer.

In another aspect, this disclosure features a system for performing local registration using fluoroscopy. The system may include a processor in communication with a fluoroscope and a memory that stores a neural network and instructions that, when executed by the processor, cause the processor to: acquire fluoroscopic images of at least an anatomical structure and a medical device in a patient's body; process the fluoroscopic images with a neural network; determine the orientation of the patient's body in the fluoroscopic images based on the results of processing the fluoroscopic images with the neural network; generate a three-dimensional (3D) reconstruction of the fluoroscopic images based on at least the orientation of the determined orientation candidate; and perform local registration based on the 3d reconstruction.

Implementations may include one or more of the following features. The instructions, when executed by the processor, may further cause the processor to generate and display a fluoroscopic computed tomography image derived from the 3d reconstruction. The instructions, when executed by the processor, may further cause the processor to acquire a sequence of fluoroscopic images of at least a medical device in a patient's body, train the neural network using a first portion of the sequence of fluoroscopic images, and validate the neural network using a second portion of the sequence of fluoroscopic images. The neural network may incorporate orientation candidates. The orientation candidates may include flip candidates. The flip candidates, for example, may include: (1) head up, right arm left, (2) head up, right arm left, (3) head down, right arm left, and (4) head down, right arm right.

In still another aspect, this disclosure features a method for detecting an orientation of a patient's body in a sequence of frames of fluoroscopic images. The method includes acquiring the sequence of frames of the fluoroscopic images from a fluoroscopic sweep of the patient's body; processing the fluoroscopic image frames with a convolutional neural network to obtain probability values for orientation candidates; for each fluoroscopic image frame in a subset of the frames of fluoroscopic images, selecting an orientation candidate having a highest probability value; and determining that the orientation of the patient's body corresponds to the orientation candidate that is selected the greatest number of times.

Implementations may include one or more of the following features. The method may include: determining a confidence level based on a may include of probability values throughout the frames of fluoroscopic images; determining that the confidence level is greater than a threshold; and in response to determining that the confidence level is greater than the threshold, generating a three-dimensional (3D) reconstruction of the frames of fluoroscopic images based on at least the determined orientation. The method may include: determining that the confidence level is not greater than the threshold; and in response to determining that the confidence level is not greater than the threshold, requesting a user to confirm the determined orientation.

BRIEF DESCRIPTION OF THE DRAWINGS

Various exemplary embodiments are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

As described above, during setup of the fluoroscope for local registration, the fluoroscope is positioned above the patient, a fluoroscopic image is captured, the orientation of the fluoroscopic image is determined and manually set by the clinician by selecting appropriate image labels corresponding to the orientation of the patient's body in the fluoroscopic image. However, this manual step is prone to human error. For example, clinicians often cannot tell what the orientation of a lung is by looking at the fluoroscope or fluoroscopic images captured by the fluoroscope.

The disclosure is directed to systems and methods for automatic detection of fluoroscopic image orientation based on deep learning models including a neural network. The neural network may be trained and validated using a sequence of fluoroscopic images, e.g., fluoroscopic images from a fluoroscopic sweep. The trained neural network receives a fluoroscopic image frame, extracts features, and classifies the fluoroscopic image frame to one of multiple candidate orientation options, e.g., candidate flip options. To achieve more robust classification, the neural network may be applied on multiple fluoroscopic image frames from a fluoroscopic sweep and the results are combined to obtain a final decision as to the orientation of in the fluoroscopic image frames. Applying the neural network multiple times on a single fluoroscopic sweep allows for estimation of the classification uncertainty. In high uncertainty cases, the systems and methods of the disclosure may prompt the user for confirmation of the orientation of the patient's body in the fluoroscopic images of the fluoroscopy sweep.

Figure 1:
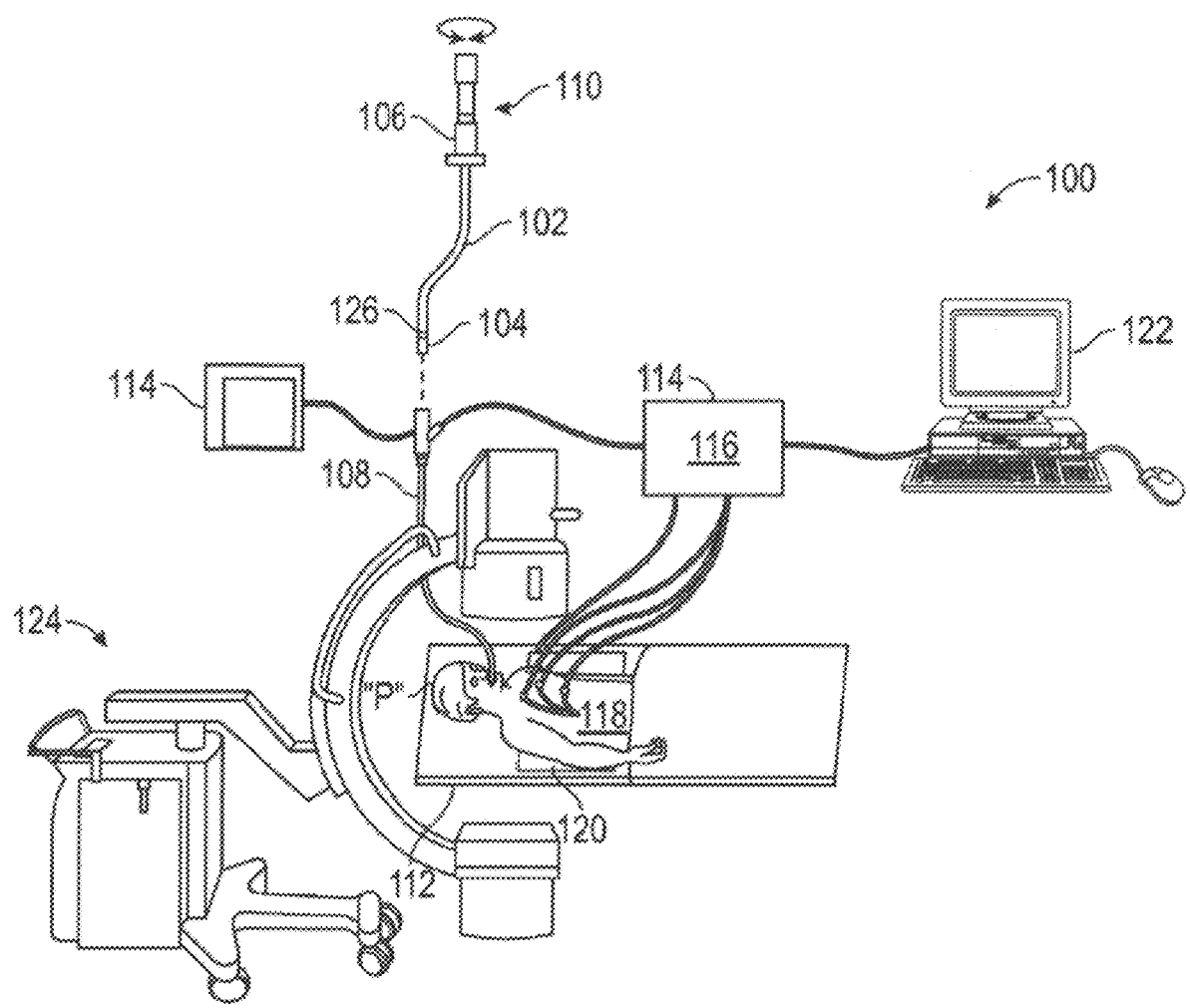
FIG. 1 is a schematic diagram of a system configured for use with the method of the disclosure.

FIG. 1 is a perspective view of an exemplary system 100 for navigation of a medical device, e.g., a biopsy or treatment tool, to a target via airways of the lungs. One aspect of the system 100 is a software application for reviewing computed tomography (CT) image data that has been acquired separately from system 100. The review of the CT image data allows a user to identify one or more targets and plan a pathway to an identified target. This is typically referred to as a planning phase. Another aspect of the software application is a navigation phase which allows a user to navigate a catheter or other tool to a target (navigation phase) using a user interface and confirm placement of the catheter or a tool relative to the target. Local registration may be performed during the navigation phase so that the clinician can more accurately see in displayed medical images the placement of the catheter or tool relative to the target. The target is typically tissue of interest for biopsy or treatment that was identified during the planning phase by review of the CT image data.

Following navigation, a medical device, such as a biopsy tool or treatment tool, may be inserted into the catheter to obtain a tissue sample from the tissue located at, or proximate to, the target or to treat such tissue. The treatment tool may be selected to achieve microwave ablation, radiofrequency ablation, cryogenic ablation, chemical ablation, or other treatment mechanism of the target as preferred by the clinician.

One aspect of FIG. 1 is a catheter guide assembly 102 including a sensor 104 at a distal end. The catheter guide assembly 102 includes a catheter 106. In practice, catheter 106 is inserted into a bronchoscope 108 for access to a luminal network of the patient P. Specifically, catheter 106 of catheter guide assembly 102 may be inserted into a working channel of bronchoscope 108 for navigation through a patient's luminal network. If configured for electromagnetic navigation (EMN) (as described below), a locatable guide (LG) 110, which may include the sensor 104 such as an electromagnetic (EM) sensor may be inserted into catheter 106 and locked into position such that sensor 104 extends a desired distance beyond the distal tip of catheter 106. However, the sensor 104 may be incorporated into one or more of the bronchoscope 108, catheter 106, or a biopsy or treatment tool, without departing from the scope of the disclosure.

If the catheter 106 is inserted into the bronchoscope 108, the distal end of the catheter 106 and LG 110 both extend beyond the distal end of the bronchoscope 108. The position or location and orientation of sensor 104 and thus the distal portion of LG 110, within an electromagnetic field can be derived based on location data in the form of currents produced by the presence of the EM sensors in a magnetic field, or by other means described herein. Though the use of EM sensors and EMN are not required as part of this disclosure, their use may further augment the utility of the disclosure in endoluminal navigation (e.g., navigation of the lungs). In some aspects, the EM sensors may be used to determine in which anatomical or sub-anatomical regions the catheter 106 is located when determining the orientation of a patient's body in fluoroscopic images, as described in more detail below. As the bronchoscope 108, catheter 106, LG 110 or other tool could be used interchangeably or in combination herein, the term catheter will be used here to refer to one or more of these elements. Further, as an alternative to the use of EM sensors, flex sensors such as fiber Bragg sensors, ultrasound sensors, accelerometers, and others may be used in conjunction with the disclosure to provide outputs to the tracking system 114 for determination of the position of a catheter including without limitation the bronchoscope 108, catheter 106, LG 110, or biopsy or treatment tools, without departing from the scope of the disclosure.

System 100 may generally include an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108). If configured for EMN, system 100 may include a locating or tracking system 114 and a locating module 116, reference EM sensors 118 and a transmitter mat 120 including radio-opaque or partially radio-opaque markers. Other patterns, including three dimensional markers at different relative depths in the transmitter mat 120, or a non-repeating pattern may be employed without departing from the scope of the disclosure.

Also included is a computing device 122 including software and/or hardware used to facilitate identification of a target, pathway planning to the target, navigation of a medical device to the target, local registration, and/or confirmation and/or determination of placement of catheter 106, or a suitable device therethrough, relative to the target. Computing device 122 may be similar to workstation 801 of FIG. 8 and may be configured to execute the methods of the disclosure including the methods of FIGS. 5-7. Computing device 122 may be any suitable computing device including a processor and storage medium, wherein the processor is capable of executing instructions stored on the storage medium as one or more applications. Computing device 122 may further include a database configured to store patient data, CT data sets including CT images, fluoroscopic data sets including fluoroscopic images and video (e.g., fluoroscopic images from a fluoroscopic sweep), fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed. Further details of the computing device are described in connection with FIG. 8 below.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images and CT image data sets acquired from CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s).

As noted above a fluoroscopic imaging device 124 capable of acquiring fluoroscopic or x-ray images or video of the patient P (fluoroscopic image data sets) is also included in system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from multiple different angles or perspectives relative to patient P to create a sequence of fluoroscopic images, such as a fluoroscopic sweep or a fluoroscopic video. The pose of fluoroscopic imaging device 124 relative to patient P may be estimated using the markers 121. The pose estimation process may be undertaken for every image or a portion of the images in the fluoroscopic sweep or video. The result of the processing is a determination of the pose of the fluoroscopic imaging device 124 for each acquired fluoroscopic image. Also, the orientation of a patient's body captured in fluoroscopic images may be determined using the image processing techniques described hereinbelow. The pose estimation data and patient orientation data, as well as other necessary data, can be used to generate the 3D reconstruction and, where desired, to register the 3D reconstruction to a 3D model generated from a pre-operative CT scan.

The markers 121 may be incorporated into the transmitter mat 120, incorporated into the operating table 112, or otherwise incorporated into another appliance placed on or near the operating table 112 so that they can be seen in the fluoroscopic images. The markers 121 are generally positioned under patient P and between patient P and a radiation source or a sensing unit of fluoroscopic imaging device 124. Fluoroscopic imaging device 124 may include a single imaging device or more than one imaging device.

Figure 2:
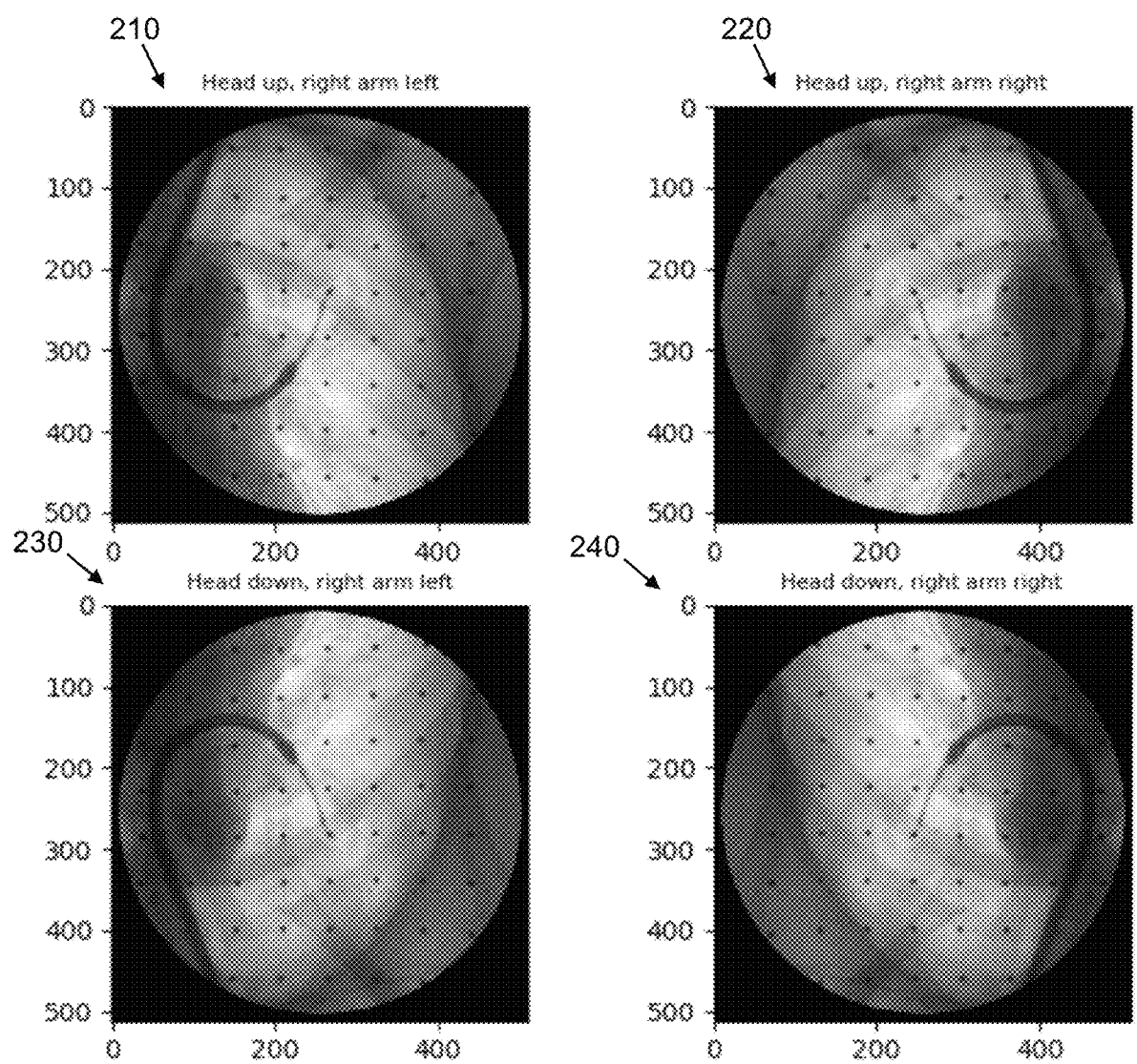
FIG. 2 are examples of fluoroscopic images at different orientations in accordance with one aspect of the disclosure.

During local registration, the fluoroscopic imaging device 124 may output one of the fluoroscopic images 210-240 shown in FIG. 2 depending, for example, on the output settings, e.g., flip settings, of the fluoroscopic imaging device 124, the brand of the fluoroscopic imaging device 124, and/or the position of the fluoroscope with respect to the patient's bed. In some aspects, the fluoroscopic imaging device 124 may output fluoroscopic images in which the orientation of the patient's body corresponds to the orientation of a patient's body shown in one of the fluoroscopic images 210-240 of FIG. 2. The orientation of the patient's body in fluoroscopic image 210 is head up, right arm left; the orientation of the patient's body in fluoroscopic image 220 is head up, right arm right; the orientation of the patient's body in fluoroscopic image 230 is head down, right arm left;

and the orientation of the patient's body in fluoroscopic image 240 is head down, right arm right. The orientation of the patient's body in the fluoroscopic images is needed to correctly generate a 3D fluoroscopic reconstruction. In some aspects, the disclosure features systems and methods that can automatically detect the orientation of a patient's body in a fluoroscopic image based on candidate orientations of a patient's body as illustrated in the fluoroscopic images 210-240 shown in FIG. 2.

Aspects of the disclosure use deep learning to classify orientations of a patient's body in fluoroscopic images. For example, fluoroscopic images may be classified using a neural network. The neural network may include a feature extraction layer and a classification layer. In the feature extraction layer, an input fluoroscopic image is processed by multiple convolution layers. Each convolution layer is followed by a non-linear operation and sampling operations. In the classification layer, the output of the feature extraction layer is processed by one or more additional layers and outputs a probability value for each possible output class. The output classes are different possible patient body orientations in a fluoroscopic image.

Figure 3:
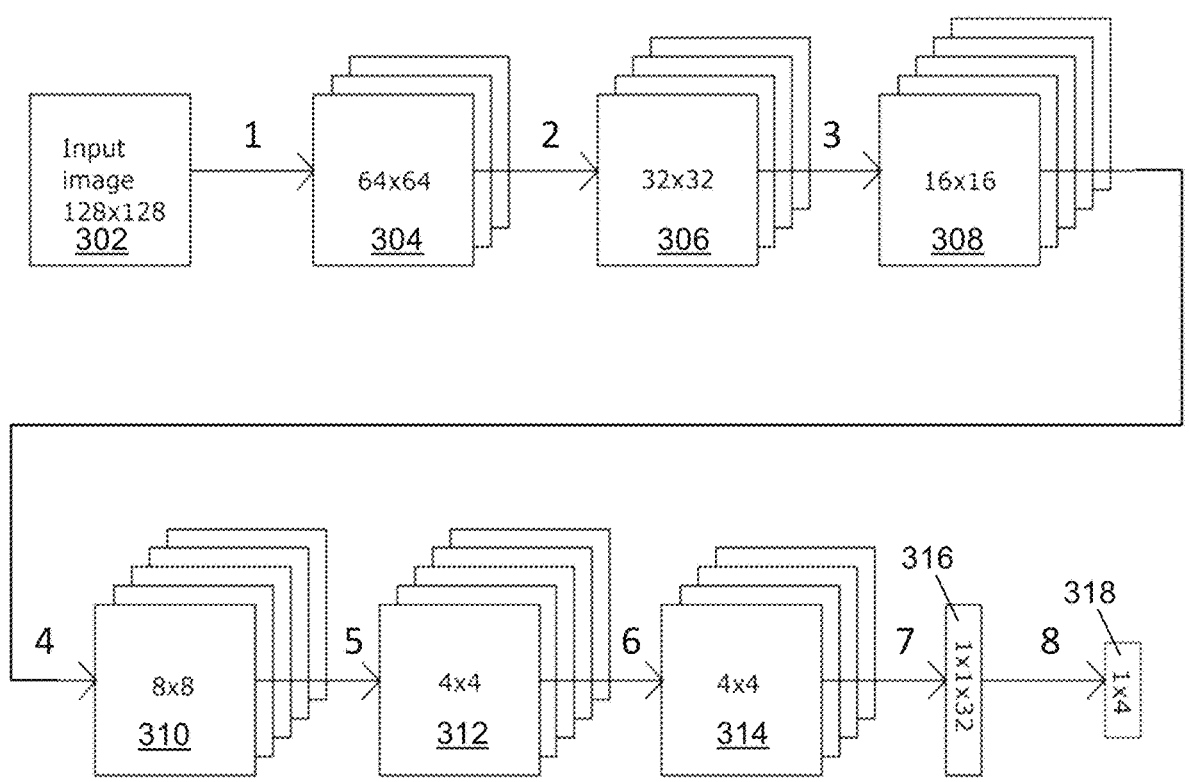
FIG. 3 is a flow diagram of a convolutional neural network model in accordance with an aspect of the disclosure.

FIG. 3 is a network diagram illustrating an example of a neural network model which may be used to the classify input fluoroscopic images as one of different orientation or flip candidates according to some aspects. The indicated sizes of the input fluoroscopic image, the kernels, the activation maps, the fully connected layer, and other features of the neural network model of FIG. 3 are not intended to be limiting, but are intended to illustrate of one of many ways to implement a neural network according to aspects of the disclosure. Steps 1-7 relate to the feature extraction layer of the neural network model and step 8 relates to the classification layer of the neural network model. At step 1, an input fluoroscopic image 302 is processed by a first processing layer, which may include a first convolutional layer, a batch normalization layer, a rectified linear unit (ReLU) layer, and a maximum pooling layer. The first convolutional layer may include 1 input channel and 16 output channels, and may use a 7×7 pixel kernel. The outputs from the first processing layer are 16 64×64 pixel activation maps 304. At step 2, the 16 64×64 pixel activation maps 304 are processed by a second processing layer, which may include a second convolutional layer, a batch normalization layer, a rectified linear unit (ReLU) layer, and a maximum pooling layer. The second convolutional layer may include 16 input channels and 32 output channels, and may use a 5×5 pixel kernel. The outputs from the second convolutional layer are 32 32×32 pixel activation maps 306.

At step 3, the 32 32×32 pixel activation maps 306 are processed by a third processing layer, which may include a third convolutional layer, a batch normalization layer, a rectified linear unit (ReLU) layer, and a maximum pooling layer. The third convolutional layer may include 32 input channels and 64 output channels, and may use a 3×3 pixel kernel. The outputs from the third convolutional layer are 64 16×16 pixel activation maps 308.

At step 4, the 64 16×16 pixel activation maps 308 are processed by a fourth processing layer, which may include a fourth convolutional layer, a batch normalization layer, a rectified linear unit (ReLU) layer, and a maximum pooling layer. The fourth convolutional layer may include 64 input channels and 64 output channels, and may use a 3×3 pixel kernel. The outputs from the fourth convolutional layer are 64 8×8 pixel activation maps 310.

At step 5, the 64 8×8 pixel activation maps 310 are processed by a fifth processing layer, which may include a fifth convolutional layer, a batch normalization layer, a rectified linear unit (ReLU) layer, and a maximum pooling layer. The fifth convolutional layer may include 64 input channels and 64 output channels, and may use a 3×3 pixel kernel. The outputs from the fifth convolutional layer are 64 4×4 pixel activation maps 312.

At step 6, the 64 4×4 pixel activation maps 312 are processed by a sixth processing layer, which may include a sixth convolutional layer, a batch normalization layer, and a rectified linear unit (ReLU) layer. The sixth convolutional layer may include 64 input channels and 32 output channels, and may use a 1×1 pixel kernel. The outputs from the sixth processing layer are 32 4×4 pixel activation maps 314. At step 7, the 32 4×4 pixel activation maps 314 are processed by a seventh processing layer, which may include an average pooling layer. The output from the seventh processing layer is a 1×1×32 feature array 316. At step 8, the 1×1×32 feature array 316 is processed by an eighth processing layer, which includes a fully connected layer with 32 inputs and 4 outputs corresponding to four flip candidates, a softmax processing layer, and an array of probability values 318 corresponding to the four flip candidates.

Figure 4:
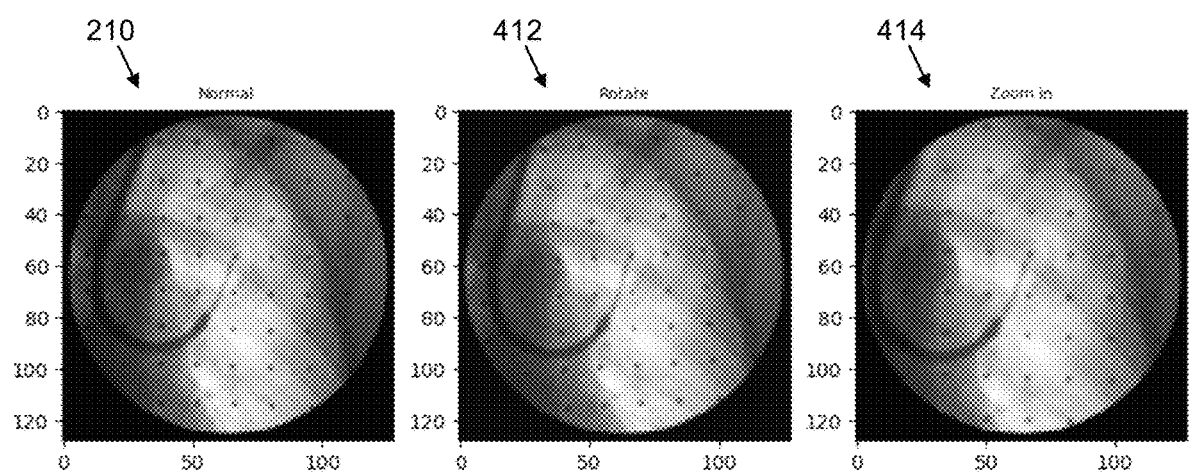
FIG. 4 are examples of fluoroscopic images illustrating how fluoroscopic images may be modified to improve orientation detection in accordance with aspects of the disclosure.

In aspects, the fluoroscopic images used to train the convolutional neural network may be preprocessed to improve or optimize the image orientation detection by the convolutional neural network. For example, as illustrated in FIG. 4, a fluoroscopic image 210 used for training may be rotated to obtain a rotated fluoroscopic image 412. In aspects, the fluoroscopic image 210 used for training may be rotated between −5 degrees and +5 degrees.

In aspects, the fluoroscopic images input to a trained and validated convolutional neural network to detect the orientation of the fluoroscopic images may be preprocessed to improve or optimize the performance of the image orientation detection by the convolutional neural network. For example, as also illustrated in FIG. 4, a zoom in or enlargement process may be applied to a fluoroscopic image 210 to obtain an enlarged fluoroscopic image 414, which may then be applied to the trained and validated convolutional network to determine the patient's orientation in the fluoroscopic image 414.

Figure 5:
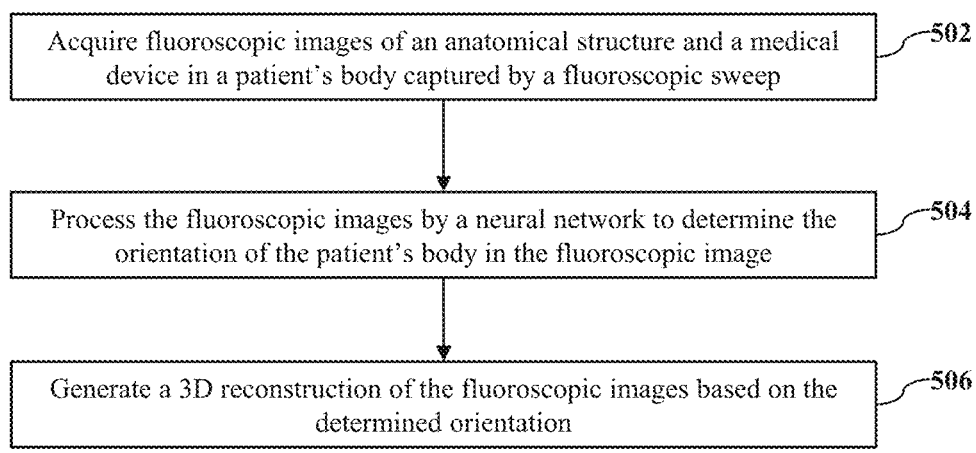
FIG. 5 is a flowchart of a method of detecting an orientation of a patient's body in fluoroscopic images using a neural network in accordance with an aspect of the disclosure.

As part of a navigation procedure, a medical device, e.g., a catheter 106, is navigated to a desired location in the patient "P." This may be done by following the pathway plan and the EM system described above or under bronchoscopic imaging or under fluoroscopic imaging using fluoroscopic imaging device 124. Having navigated the catheter 106 to a desired location, a fluoroscopic sweep can be performed. This fluoroscopic sweep acquires 2D fluoroscopic images at multiple different angles as the fluoroscopic imaging device 124 rotates about the patient "P." FIG. 5 is a flowchart of a method 700 of detecting an orientation of a patient's body in the acquired 2D fluoroscopic images using a neural network model and using the detected orientation to generate a 3D reconstruction of the fluoroscopic images in accordance with an aspect of the disclosure. At block 502, fluoroscopic images of an anatomical structure and a medical device in a patient's body captured by a fluoroscopic sweep are acquired. At block 504, the fluoroscopic images are processed by a neural network to determine the orientation of the patient's body in the fluoroscopic image. And at block 506, a 3D reconstruction of the fluoroscopic images is generated based on the determined orientation.

In order to improve the neural network, it must be trained to detect the orientation of the patient's body. The neural network is trained in a supervised manner. The training set may include thousands of fluoroscopy 2D images showing a target and a medical device.

Figure 6:
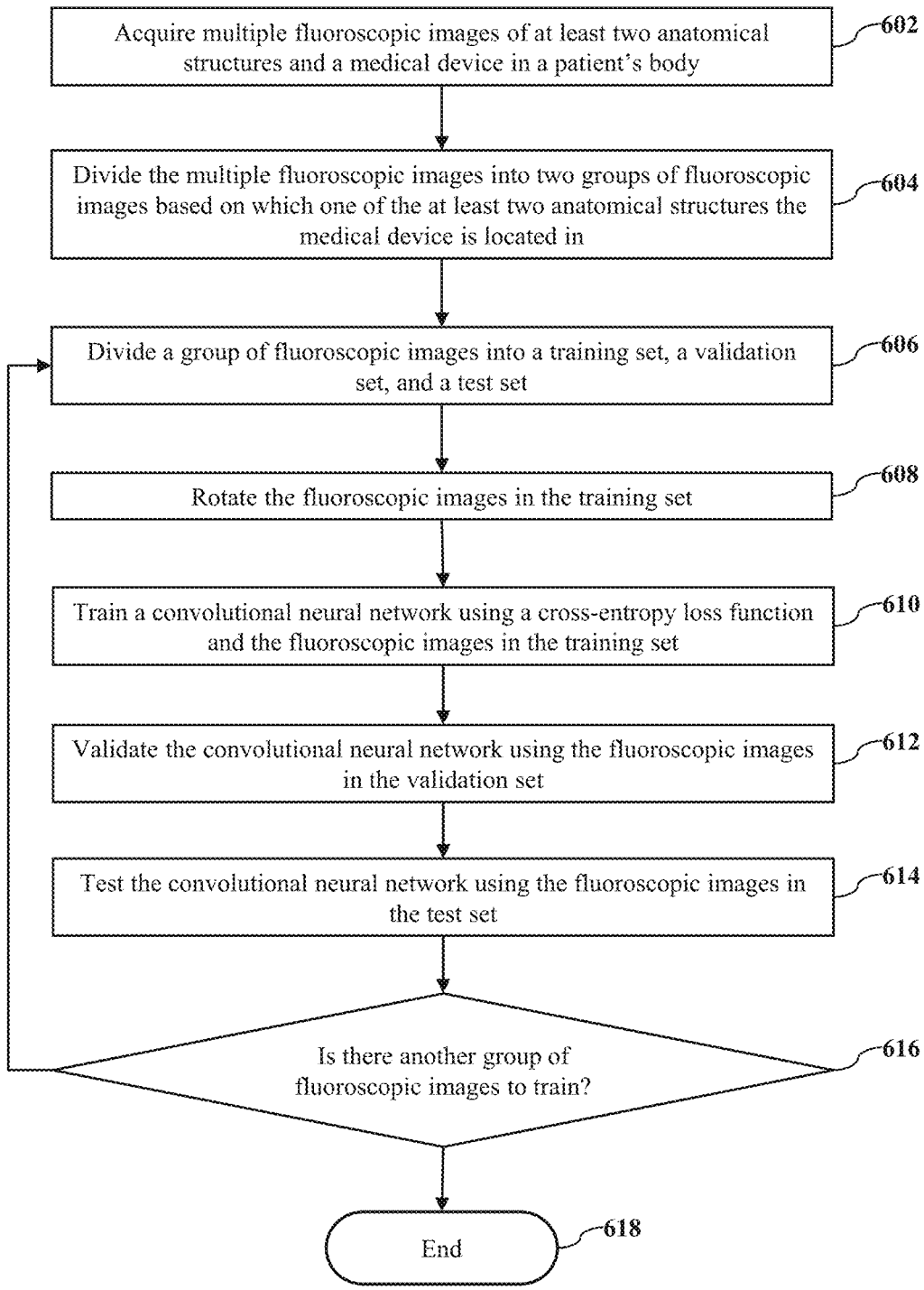
FIG. 6 is a flowchart of a method of training a neural network model in accordance with an aspect of the disclosure.

FIG. 6 is a flow diagram of an example of one method 600 for training a neural network model in accordance with an aspect of the disclosure. This training method is not meant be limiting, but is one example of how a neural network may be trained. At block 602, multiple fluoroscopic images of a target and a medical device in a patient's body is acquired. The multiple fluoroscopic images may be obtained by performing multiple fluoroscopic sweeps. In some aspects, the clinician may position the fluoroscope perpendicular to the patient's bed, which may include a grid of markers, prior to performing multiple fluoroscopic sweeps.

At block 604, the multiple fluoroscopic images are divided into two groups of fluoroscopic images based on which one of a pair of anatomical features the medical device is located in. At block 606, a group of fluoroscopic images is divided into a training set, a validation set, and a test set. At block 608, the fluoroscopic images in the training set are rotated by a small angle, e.g., 3 degrees. Alternatively, or additionally, the fluoroscopic images in the training set may be enlarged or processed by a zoom-in operation. At block 610, a convolutional neural network model is trained using a cross-entropy loss function and the fluoroscopic images in the training set. In other aspects, the cross-entropy loss function may be replaced by any loss function suitable for training a neural network to detect an orientation of a patient in fluoroscopic images. For example, the cross-entropy loss function may be replaced by a mean squared error loss function.

At block 612, the convolutional neural network model is validated using the fluoroscopic images in the validation set, then, at block 614, the convolutional neural network model is tested using the fluoroscopic images in the test set. In aspects, the flip probability values corresponding to four flip candidates may each be set to the constant 0.25 for training and validation. At block 616, the method 600 determines whether another group of fluoroscopic images needs training. If another group of fluoroscopic images needs training, blocks 606-614 are repeated for the other group of fluoroscopic images. Otherwise, the method 600 ends at block 618.

Figure 7:
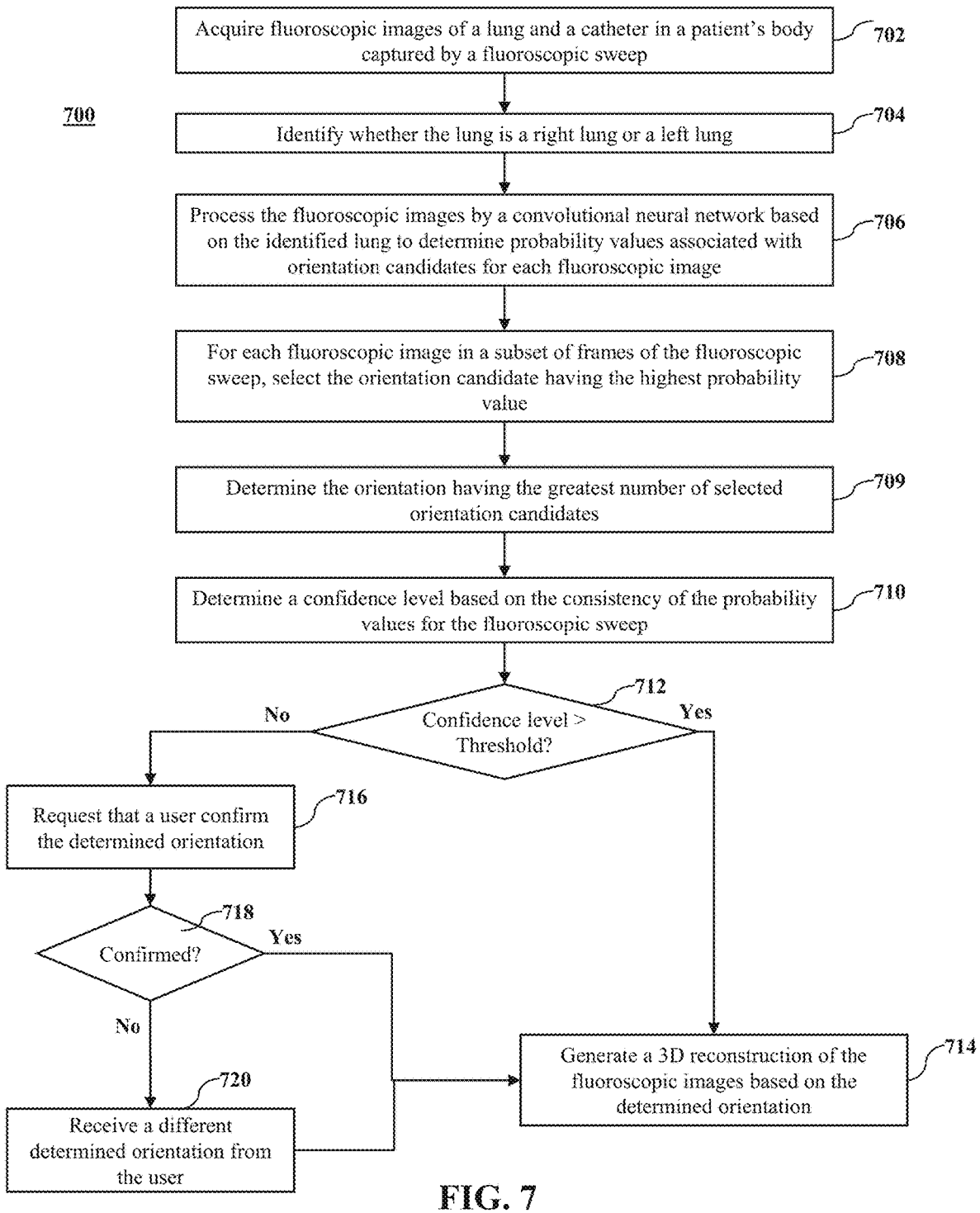
FIG. 7 is a flowchart of a method of detecting an orientation of a patient's body in fluoroscopic images using a neural network in accordance with another aspect of the disclosure.

FIG. 7 is a flow diagram of a method 700 of detecting an orientation of a patient's body in 2D fluoroscopic images using a neural network model and using the detected orientation to generate a 3D reconstruction of the 2D fluoroscopic images in accordance with an aspect of the disclosure. At block 702, the fluoroscopic images of the patient's body, which include a lung and a catheter, are acquired. In other aspects, the lung may be any anatomical structure or feature and the catheter may be any medical device suitable for a procedure involving the anatomical structure. After the fluoroscopic images are acquired, the fluoroscopic images may undergo pre-processing to improve the performance of the method including the performance of the neural network. The pre-processing may include reducing the size of the acquired fluoroscopic images.

At block 704, the lung is identified as a right lung or a left lung. The lung may be identified, for example, by determining the position of the catheter when the catheter is disposed in the lung. The position of the catheter may be determined by the EMN system described herein using an EM sensor disposed on the catheter. In other aspects, a catheter may not be needed to identify the lung as a right lung or a left lung at block 704. At block 706, taking into account the identified lung, the fluoroscopic images are processed by a convolutional neural network to determine probability values associated with orientation candidates. In some aspects, for each fluoroscopic image, an array of probability values corresponding to each orientation candidate may be generated, e.g., [0.10 0 0 0.70 0.20] for four flip orientation candidates. At block 708, for each fluoroscopic image in a subset of frames of the fluoroscopic sweep, the orientation candidate having the highest probability value is selected. At block 709, the orientation having the greatest number of selected orientation candidates is determined.

In order to improve the results of the method of FIG. 7, several post processing techniques may be employed. For example, the detection of the orientation of the patient's body in each frame of a fluoroscopic video may be given a confidence estimate or level. For example, at block 710, a confidence level based on the consistency of the probability values for the fluoroscopic sweep is estimated or determined. Next, the method 700 includes determining whether the confidence level is greater than a threshold at block 712. If the confidence level is greater than the threshold, a 3D reconstruction of the fluoroscopic images is generated based on the determined orientation at block 714.

If the confidence level is not greater than the threshold, a user is requested to confirm the determined orientation at block 716. Next, the method 700 includes determining whether the determined orientation is confirmed at block 718. If the determined orientation is confirmed, a 3D reconstruction of the fluoroscopic images is generated based on the determined orientation at block 714. If the determined orientation is not confirmed, the user is requested to input a different determined orientation at block 720 and a 3D reconstruction of the fluoroscopic images is generated based on the different determined orientation at block 714. In other aspects, if there are frames of fluoroscopic video for which the confidence estimate is low or below a predetermined threshold, the determination of the orientation of the patient's body may be rejected without performing the confirmation of blocks 716 and 718.

Figure 8:
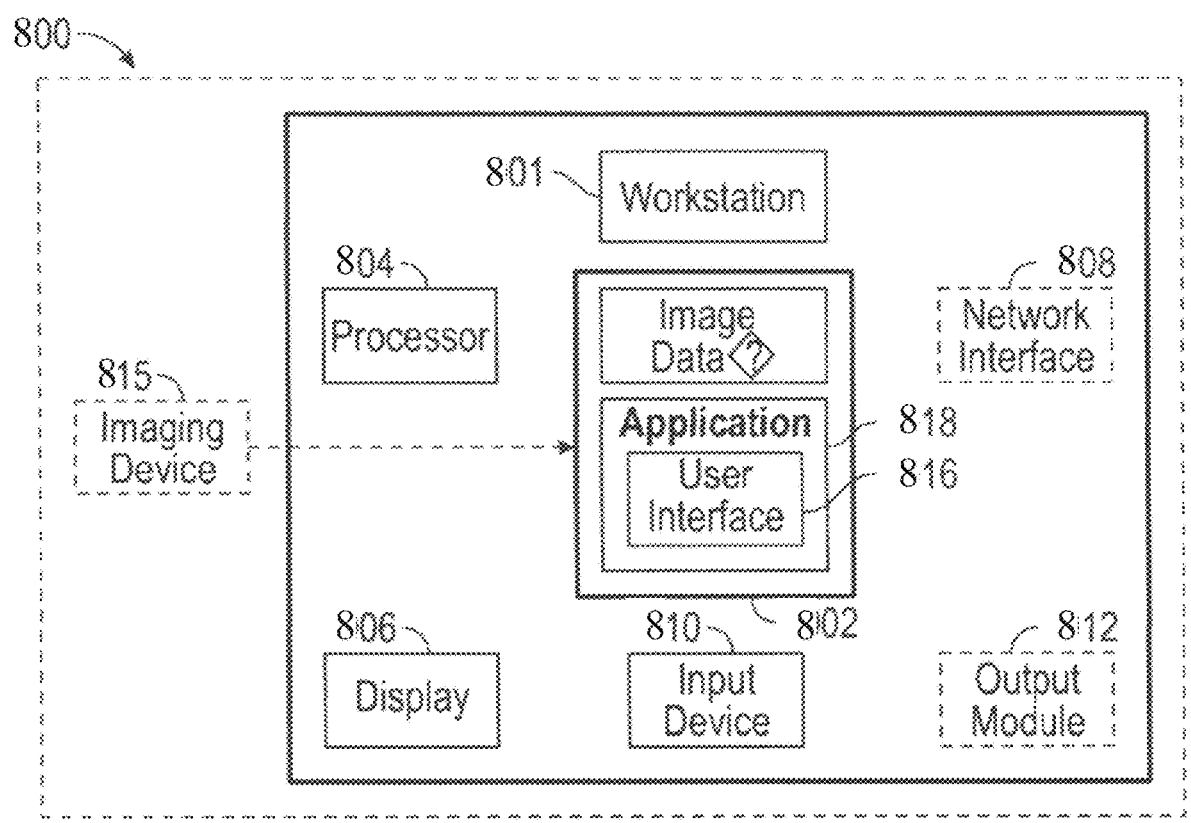
FIG. 8 is a schematic block diagram of a computing device in accordance with the disclosure.

Reference is now made to FIG. 8, which is a schematic diagram of a system 800 configured for use with the methods of the disclosure including the methods illustrated in FIGS. 3-7. System 800 may include a workstation 801, and optionally connected to fluoroscopic imaging device 124 (FIG. 1). In some embodiments, workstation 801 may be coupled with fluoroscope 815, directly or indirectly, e.g., by wireless communication. Workstation 801 may include a memory 802, a processor 804, a display 806 and an input device 810. Processor or hardware processor 804 may include one or more hardware processors. Workstation 801 may optionally include an output module 812 and a network interface 808. Memory 802 may store an application 818 and image data 814. Application 818 may include instructions executable by processor 804 for executing the methods of the disclosure including the methods and techniques of FIGS. 3-7.

Application 818 may further include a user interface 816. Image data 814 may include the CT scans, fluoroscopic images, the generated fluoroscopic 3D reconstructions and/or any other fluoroscopic image data and/or the generated one or more virtual fluoroscopy images. Processor 804 may be coupled with memory 802, display 806, input device 810, output module 812, network interface 808 and fluoroscope 815. Workstation 801 may be a stationary computing device, such as a personal computer, or a portable computing device such as a tablet computer. Workstation 801 may embed computer devices.

Memory 802 may include any non-transitory computer-readable storage media for storing data and/or software including instructions that are executable by processor 804 and which control the operation of workstation 801 and, in some embodiments, may also control the operation of fluoroscope 815. Fluoroscopic imaging device 124 may be used to capture a sequence of fluoroscopic images based on which the fluoroscopic 3D reconstruction is generated and to capture a live 2D fluoroscopic view according to this disclosure. In an embodiment, memory 802 may include one or more storage devices such as solid-state storage devices, e.g., flash memory chips. Alternatively, or in addition to the one or more solid-state storage devices, memory 802 may include one or more mass storage devices connected to the processor 804 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 804. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 801.

Application 818 may, when executed by processor 804, cause display 806 to present user interface 816. User interface 816 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view, a 3D reconstruction of fluoroscopic images of a fluoroscopic sweep, as well as other images and screens. User interface 816 may be further configured to display the target mark in different colors depending on whether the medical device tip is aligned with the target in three dimensions.

Network interface 808 may be configured to connect to a network such as a local area network (LAN) consisting of a wired network and/or a wireless network, a wide area network (WAN), a wireless mobile network, a Bluetooth network, and/or the Internet. Network interface 808 may be used to connect between workstation 801 and fluoroscope 815. Network interface 808 may be also used to receive image data 814. Input device 810 may be any device by which a user may interact with workstation 801, such as, for example, a mouse, keyboard, foot pedal, touch screen, and/or voice interface. Output module 812 may include any connectivity port or bus, such as, for example, parallel ports, serial ports, universal serial busses (USB), or any other similar connectivity port known to those skilled in the art.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

What is claimed is:

1. A method comprising:
acquiring fluoroscopic images of at least one anatomic feature and a medical device in a patient's body captured by performing a fluoroscopic sweep with a fluoroscopic imaging device;
processing the fluoroscopic images by a neural network;
determining an orientation of the patient's body in the fluoroscopic images based on the processing of the fluoroscopic images by the neural network classifying the fluoroscopic images into one of multiple patient orientation candidates, yielding a determined orientation, wherein each of the fluoroscopic images from the fluoroscopic sweep are processed using the neural network and results of the processing are combined to determine the orientation of the patient's body in the fluoroscopic images;
estimating a pose of the fluoroscopic imaging device relative to the patient, yielding an estimated pose; and
generating a three-dimensional (3D) reconstruction of the fluoroscopic images based on at least the estimated pose and the determined orientation of the patient's body in the fluoroscopic images.

2. The method of claim 1, wherein the at least one anatomic feature is a sub-anatomical region, further comprising:
acquiring position information of the medical device in the sub-anatomical region from an electromagnetic sensor disposed on the medical device;
identifying the sub-anatomical region based on the position information, yielding an identified sub-anatomical region; and
processing the fluoroscopic images by a trained neural network based on the identified sub-anatomical region to determine the orientation of the patient's body in the fluoroscopic images.

3. The method of claim 2, wherein the fluoroscopic images form a portion of a fluoroscopic sweep.

4. The method of claim 3, wherein a subset of the fluoroscopic images is processed by the neural network.

5. The method of claim 2, further comprising resizing the fluoroscopic images.

6. The method of claim 2, wherein the sub-anatomical region is a lobe of a lung.

7. The method of claim 2, wherein the medical device is a navigation catheter and the electromagnetic sensor forms part of an electromagnetic navigation system.

8. The method of claim 1, wherein the neural network is a convolutional neural network including convolutional layers, batch normalization layers, rectified linear unit layers, maximum pooling layers, an average pooling layer, and a fully connected layer.

9. The method of claim 1, wherein the processing includes, for each fluoroscopic image of the fluoroscopic images:
generating a probability value for patient orientation candidates; and
selecting the patient orientation candidate having a highest probability value.

10. The method of claim 9, wherein the patient orientation candidates are four flip candidates.

11. A system for performing local registration using fluoroscopy comprising:
a processor in communication with a fluoroscope; and
a memory configured to store a neural network and instructions that, when executed by the processor, cause the processor to:

acquire fluoroscopic images of at least an anatomical structure and a medical device from a fluoroscopic sweep of a patient's body with a fluoroscopic imaging device;

process the fluoroscopic images with a neural network;

determine a patient orientation candidate for an orientation of the patient's body in the fluoroscopic images based on results of processing the fluoroscopic images with the neural network classifying the fluoroscopic images into one of multiple patient orientation candidates, yielding a determined orientation, wherein each of the fluoroscopic images from the fluoroscopic sweep are processed using the neural network and the results of the processing are combined to determine the orientation of the patient's body in the fluoroscopic images;

estimate a pose of the fluoroscopic imaging device relative to the patient, yielding an estimated pose;

generate a three-dimensional (3D) reconstruction of the fluoroscopic images based on at least the estimated pose and the orientation of the patient orientation candidate; and perform local registration based on the 3D reconstruction.

12. The system of claim 11, wherein the instructions, when executed by the processor, further cause the processor to generate and display a fluoroscopic computed tomography image derived from the 3D reconstruction.

13. The system of claim 11, wherein the instructions, when executed by the processor, further cause the processor to:

acquire a sequence of fluoroscopic images of at least a medical device in a patient's body;

train the neural network using a first portion of the sequence of fluoroscopic images; and validate the neural network using a second portion of the sequence of fluoroscopic images.

14. The system of claim 13, wherein the multiple patient orientation candidates include flip candidates.

15. The system of claim 14, wherein the flip candidates include: (1) head up, right arm left, (2) head up, right arm left, (3) head down, right arm left, and (4) head down, right arm right.

16. A method for detecting an orientation of a patient's body in a sequence of frames of fluoroscopic images, the method comprising:

acquiring the sequence of frames of the fluoroscopic images from a fluoroscopic sweep of the patient's body;

processing the fluoroscopic image frames with a convolutional neural network to obtain probability values for orientation candidates;

for each fluoroscopic image frame in a subset of the frames of fluoroscopic images, selecting an orientation candidate having a highest probability value;

determining that the orientation of the patient's body corresponds to the orientation candidate that is selected the greatest number of times;

determining a confidence level based on a consistency of probability values throughout the frames of fluoroscopic images;

determining that the confidence level is greater than a threshold; and in response to determining that the confidence level is greater than the threshold, generating a three-dimensional (3D) reconstruction of the frames of fluoroscopic images based on at least the determined orientation.

17. The method of claim 16, further comprising:

determining that the confidence level is not greater than the threshold; and in response to determining that the confidence level is not greater than the threshold, requesting a user to confirm the determined orientation.

* * * * *